(12) United States Patent
Howley et al.

(10) Patent No.: US 7,569,228 B2
(45) Date of Patent: Aug. 4, 2009

(54) FUSION PROTEINS OF NON-ATTENUATED HIV REGULATORY/ACCESSORY PROTEINS

(75) Inventors: Paul Howley, Glen Waverly (GB); Sonja Leyer, Munich (DE); Eva Felder, Munich (DE)

(73) Assignee: Bavarian Nordic A/S, Kvistgaard (DK)

( * ) Notice: Subject to any disclaimer, the term of this patent is extended or adjusted under 35 U.S.C. 154(b) by 0 days.

(21) Appl. No.: 11/488,803

(22) Filed: Jul. 18, 2006

(65) Prior Publication Data

US 2006/0257974 A1 Nov. 16, 2006

Related U.S. Application Data

(62) Division of application No. 10/514,740, filed as application No. PCT/EP03/05039 on May 14, 2003, now abandoned.

(30) Foreign Application Priority Data

May 16, 2002 (DK) .............................. 2002 00754

(51) Int. Cl.
*A61K 39/12* (2006.01)
*A61K 39/21* (2006.01)
*A61K 39/275* (2006.01)
(52) U.S. Cl. ............... 424/199.1; 424/208.1; 424/232.1
(58) Field of Classification Search ................ 536/23.1, 536/23.72; 435/320.1; 424/192.1, 199.1
See application file for complete search history.

(56) References Cited

U.S. PATENT DOCUMENTS

2002/0015707 A1* 2/2002 Rutter et al. ............. 424/184.1
2005/0260156 A1* 11/2005 Suter et al. ................. 424/85.7

FOREIGN PATENT DOCUMENTS

| WO | WO 99/16884 | 4/1999 |
| WO | WO 99/27958 | 6/1999 |
| WO | WO 99/43841 | 9/1999 |
| WO | WO 01/54719 | 8/2001 |
| WO | WO 01/92470 | 12/2001 |
| WO | WO 02/04493 | 1/2002 |
| WO | WO 02/06303 | 1/2002 |
| WO | WO 02/36806 | 5/2002 |

OTHER PUBLICATIONS

Kusumi et al. Human immunodeficiency virus type 1 envelope gene structure and diversity in vivo and after cocultivation in vitro. Journal of Virology, Feb. 1992, vol. 66, No. 2, p. 875-885.*

Meyerhans et al. Temporal fluctuations in HIV quasispecies in vivo are not reflected by sequential HIV isolations. Cell 1989, vol. 58, p. 901-910.*
Rossi et al. Ribozymes as anti-HIV-1 therapeutic agents: principles, applications, and problems. AIDS research and human retroviruses Feb. 1992, vol. 8, No. 2, p. 183-189. Abstract only.*
Derosiers. Prospects for an AIDS vaccine: Nature Medicine Mar. 2004, vol. 10, No. 3, p. 221-223.*
Leslie et al. HIV evolution: CTL escape mutation and reversion after transmission. Nature Medicine Mar. 2004 vol. 10, No. 3, p. 282-289.*
Altman et al. HIV escape: there and back again. Nature Medicine Mar. 2004 vol. 10, No. 3, p. 229-230.*
Friedrich et al. Reversion of CTL escape—variant immunodeficiency viruses in vivo. Nature Medicine Mar. 2004 vol. 10, No. 3, p. 275-281.*
"Immunogenicity of a Novel and Vaccine Cassette expressing multiple human immunodeficiency virus (HIV-1) accessory genes", Velpandi Ayyavoo et al.; *AIDS* 14(1):1-9 (2000).
"DNA vaccination in mice using HIV-1 nef, rev and tat genes in self-replicating pBN-vector.", Tahtinen et al.,: *Vaccine* 19:2039-2047 (2001).
"Control of a Mucosal Challenge and Prevention of AIDS by a multiprotein DNA/MVA vaccine", Amara et al., *Science* 292:69-74 (2001).
"Activation of transcription by HIV-1 TAT protein tethered to nascent RNA through another protein", Southgate, *Nature* 345:640-642 (1990).
"Construction of attenuated HIV-1 accessory gene immunization cassettes", Ayyavoo et al., *Vaccine* 16:1872-1879 (1998).
"Recognition of Prominent Viral Epitopes Induced by Immunization with Human Immunodeficiency Virus Type 1 Regulatory Genes", Hinkula et al., *J. Virology* 71:5528-5539 (1997).
"Membrane-Fusing Capacity of the Human Immunodeficiency Virus Envelope Proteins Determines the Efficiency of CD4+ T-Cell Depletion in Macaques Infected by a Simian-Human Immunodeficiency Virus" Etemad-Moghadam et al., J. Virology 75:5645-5655 (2001).

\* cited by examiner

*Primary Examiner*—Jeffrey S. Parkin
*Assistant Examiner*—Louise Humphrey
(74) *Attorney, Agent, or Firm*—Law Office of Salvatore Arrigo (57) ABSTRACT

Nucleic acids are disclosed encoding fusion proteins comprising the amino acid sequence of at least four non-attenuated HIV proteins selected from the group consisting of Vif, Vpr, Vpu, Vpx, Rev, Tat, and Nef, wherein the fusion protein does not contain a specific cleavage sequence for a cellular protease. Also disclosed are vectors comprising the nucleic acids and methods of preparing the fusion protein by transfecting a host cell with the nucleic acids or with the vectors containing the nucleic acids, expressing the fusion proteins, and recovering the fusion proteins.

8 Claims, 4 Drawing Sheets

FUSION PROTEINS OF NON-ATTENUATED HIV REGULATORY/ACCESSORY PROTEINS

CROSS REFERENCE TO RELATED APPLICATIONS

This application is a divisional of Ser. No. 10/514,740 filed 15 Nov. 2004 now abandoned, which is the U.S. National Phase of PCT Application PCT/EP03/05039 filed 14 May 2003 with a claim to the priority of Danish Patent Application PA200200754, itself filed 16 May 2002.

The invention relates to fusion proteins comprising the amino acid sequence of at least four HIV proteins selected from Vif, Vpr, Vpu, Vpx, Rev, Tat and Nef or derivatives of the amino acid sequence of one or more of said proteins, wherein the fusion protein is not processed to individual HIV proteins having the natural N and C termini. The invention further concerns nucleic acids encoding said proteins, vectors comprising said nucleic acids, and methods for producing said proteins. The fusion protein, nucleic acids and vectors are usable as vaccines for the at least partial prophylaxis against HIV infections.

BACKGROUND OF THE INVENTION

The Human Immunodeficiency virus (HIV) is the causative agent of the Acquired Immunodeficiency Syndrome (AIDS). Like all retroviruses the genome of the virus encodes the Gag, Pol and Env proteins. In addition, the viral genome encodes further regulatory proteins, i.e. Tat and Rev, as well as accessory proteins, i.e. Vpr, Vpx, Vpu, Vif and Nef.

Despite public health efforts to control the spread of the AIDS epidemic the number of new infections is still increasing. The World Health Organization estimated the global epidemic at 36.1 million infected individuals at the end of the year 2000, 50% higher than what was predicted on the basis of the data a decade ago (WHO & UNAIDS. UNAIDS, 2000). Globally, the number of new HIV-1 infections in 2000 is estimated at 5.3 million.

Given the steady spread of the epidemic, there is still a need to bring an effective vaccine to the clinic. A number of different HIV-1 vaccine delivery strategies such as novel vectors or adjuvant systems have now been developed and evaluated in different pre-clinical settings as well as in clinical trials. The first vaccine candidate that entered a phase III clinical trial is based on envelope gp 120 protein in alum (Francis et al., AIDS Res. Hum. Retroviruses 1998; 14 (Suppl 3)(5): S325-31). The phase III trials have been started although the vaccine did not prove to be too successful in the earlier phase II trial.

Following many years of prophylactic vaccine efforts based on envelope antigens, more recent efforts have focused on the use of regulatory proteins such as Tat, Nef and Rev as candidate vaccine antigens. The use of these regulatory antigens in therapeutic settings has been ongoing for several years (Miller et al., Nature Medicine 1997, 3, 389-94, Calarota et al., Lancet 1998, 351, 1320-5, Ayyavoo et al., AIDS, 2000, 14, 1-9). More recently the use of these antigens in prophylactic vaccine studies in small pre-clinical trials has revealed promise. The use of Tat and Rev, or Tat alone as a prophylactic vaccine candidate, was demonstrated to control SIVmac (Osterhaus et al., Vaccine 1999, 17, 2713-4). Moreover, there are indications that CTL directed towards the virus early regulatory proteins are important for eliminating infected cells prior to their high level production of mature virions (van Baalen et al., J. Gen. Virol 1997, 78, 1913-8; Addo et al., PNAS, 2001, 98, 1781-6).

Although the regulatory/accessory proteins of HIV induce an effective immune response, most, if not all, of them have serious side effects, which limit up to now their use as vaccine: Nef, Tat and Vpu have been shown to play a role in the down regulation of CD4+ and/or MHC class I expression (Howcroft et al., Science, 1993, 260, 1320-2; Schwartz et al., Nature Med. 1996, 2, 338-42; Swann et al., Virology, 2001, 282, 267-77; Janvier et al., J. Virol., 2001, 78, 3971-6, Weissmann et al., PNAS 1998, 95, 11601-6). It is known that Tat mediates acute immune suppression in vivo (Cohen et al., PNAS, 1999, 96, 10842-10847). Immunosuppressive effects have also been described for Vpr (Ayyavoo et al., Nature Med., 1997, 3: 1117-1123). It has been described that Vpr and Vpx have differential cytostatic and cytotoxic effects in yeast cells (Zhang et al., Virology, 1997, 230, 103-12). Thus, most, if not all accessory/regulatory proteins of HIV seem to have functional properties that are not desired in a vaccine formulation.

Attempts to reduce the harmful effects of the HIV proteins are disclosed in WO 02/06303. In particular, WO 02/06303 discloses a fusion protein including amino acid sequences of HIV Vif, Vpu and Nef, wherein the component proteins are contiguous with another component protein or separated by non-component proteins such as amino acid sequences, which make up proteolytic cleavage sites. It is disclosed that it is preferred to use those fusion proteins that comprise proteolytic cleavage sites between the component proteins. Since the component proteins are separated by proteolytic cleavage sites native HIV proteins are produced that are known to be harmful. To reduce any harmful effects of the HIV proteins that result from the cleavage of the fusion protein WO 02/06303 suggests using attenuated proteins. Thus, WO 02/06303 teaches to use a fusion protein comprising the HIV Vif, Vpr and Nef protein, wherein cleavage sites are inserted between the HIV proteins and wherein the HIV proteins are attenuated proteins. However, the disadvantage of attenuated proteins is that the amino acid sequence of the attenuated protein differs from the amino acid sequence of the native protein so that an immunization with the attenuated protein may lead to an immune response that only weakly recognizes the native protein or that even does not recognize the native protein at all.

OBJECT OF THE INVENTION

It was the object of the present invention to provide a vaccine allowing the generation of an effective immune response, in particular an effective cytotoxic T cell response, against several or all regulatory/accessory proteins of HIV, wherein the regulatory/accessory HIV proteins in the vaccine or produced by the vaccine are less functional than the native, individual regulatory/accessory proteins so that the risk is reduced that the accessory/regulatory proteins in the vaccine exert undesired side effects and wherein the less active HIV proteins induce a similar immune response than the native HIV proteins.

DETAILED DESCRIPTION OF THE INVENTION

This object has been achieved by the provision of a fusion protein comprising the amino acid sequence of at least four different HIV proteins selected from Vif, Vpr, Vpu, Vpx, Rev, Tat and Nef or derivatives of the amino acid sequence of one or more of said proteins, wherein the fusion protein is not processed to individual HIV proteins having the natural N and C termini. In particular the object of the present invention has been achieved by nucleic acids and vectors encoding said fusion proteins.

If the fusion protein is produced in animal cells, including human cells, the fusion protein is not cleaved by cellular proteases in such a way that accessory/regulatory proteins with native N- and C-termini are obtained.

Due to the fact that an HIV protein that is part of a fusion protein has an altered secondary/tertiary structure compared to the individual HIV protein, the HIV protein in the fusion protein is less functional than the individual protein, if not fully dysfunctional. A regulatory/accessory protein that is less functional or even not functional at all does not have the undesired side effects of the HIV protein in its native conformation. As far as the immunogenicity is concerned there is no substantial difference when the immunogenicity of the fusion protein is compared with the immunogenicity of the individual HIV regulatory/accessory proteins that form the fusion protein. In particular there is no substantial difference with respect to the cytotoxic T cell (CTL) response since the epitopes that are presented to the immune system are identical. The same considerations also apply if the fusion protein is administered to the patient.

In the context of the present invention the term “HIV” refers to any HIV group, subtype (clade), strain or isolate known to the person skilled in the art. In particular, HIV may be HIV-1 or HIV-2. HIV-1 has been classified in nine subtypes (clades A through I), whereas HIV-2 has been classified in five subtypes (A through E), which are all covered by the scope of the present invention. The most preferred HIV clades according to the present invention are HIV-1 clades A, B and C. However, the invention is not restricted to these most preferred clades.

The protein sequences of the HIV regulatory proteins Vif, Vpr, Vpu, Rev, Tat, Vpx and Nef are known to the person skilled in the art. By way of example and without being restricted to said embodiments reference is made to the various sequences as disclosed in the genebank database, in particular to the sequence of the HIV-1 isolate HXB2R having the genebank accession number KO3455. In this genebank entry the sequences of the various HIV1 genes and of the proteins encoded by said genes is specified.

Preferably the HIV proteins that form the fusion protein are derived from the same clade. According to an alternative embodiment the HIV proteins that form the fusion protein are derived from two or more clades. It is also possible that one or more of the HIV proteins that form the fusion protein are HIV-1 proteins and that one or more of the HIV proteins that form the fusion protein are HIV-2 proteins.

The amino acid sequences of the HIV proteins that form the fusion protein are preferably sequences that are encoded by known HIV isolates, i.e. the amino acid sequence of the HIV proteins in the fusion protein is identical to the amino acid sequences of the corresponding proteins as encoded by naturally occurring HIV isolates. Alternatively the amino acid sequence of one or more HIV proteins in the fusion protein may be a consensus sequence, i.e. a sequence that as such may not be found in a known HIV isolate but that shows an optimal homology—in particular with respect to CTL-epitopes—to several or all known HIV isolates. Computer algorithms to calculate a consensus sequence are known to the person skilled in the art.

In an alternative embodiment the fusion protein may comprise derivatives of the amino acid sequence of one or more HIV proteins that are part of the fusion protein. The term “derivative of the amino acid sequence of an HIV protein” as used in the present specification refers to HIV proteins that have an altered amino acid sequence compared to the corresponding naturally occurring HIV protein. An altered amino acid sequence may be a sequence in which one or more amino acids of the sequence of the HIV protein are substituted, inserted or deleted. More particularly a “derivative of the amino acid sequence of an HIV protein” is an amino acid sequence showing a homology of at least 50%, more preferably of at least 70%, even more preferably of at least 80%, most preferably of at least 90% when the corresponding part of the amino acid sequence in the fusion protein is compared to the amino acid sequence of the respective HIV protein of known HIV isolates. An amino acid sequence is regarded as having the above indicated sequence homology even if the homology is found for the corresponding protein of only one HIV isolate, irrespective of the fact that there might be corresponding proteins in other isolates showing a lower homology. By way of example, if a Vpr derivative in the fusion protein shows a homology of 95% to the Vpr sequence of one HIV isolate, but only a homology of 50-70% to (all) other HIV isolates, the homology of said Vpr derivative is regarded as being of at least 90%.

It has been pointed out above that the HIV proteins in the fusion protein have a reduced activity, or even no activity at all, compared to the individual proteins, since the conformation of the proteins in the fusion protein is different to the natural conformation of the biologically active proteins. However, it might be desirable to further reduce the risk that the HIV proteins in the fusion protein are biologically active. To this end particularly preferred “derivatives” of an individual HIV protein that is part of a fusion protein are amino acid sequence derivatives in which several amino acids are deleted, inserted or substituted, more preferably not more than 10 amino acids, most preferably not more than 5 amino acids to obtain an HIV protein with reduced activity or no activity at all. Tests are known to the person skilled in the art how to determine whether an HIV protein has reduced biological activity:

The molecular mechanism of the Vif protein, which is essential for viral replication in vivo, remains unknown, but Vif possesses a strong tendency toward selfassociation. This multimerization was shown to be important for Vif function in viral life cycle (Yang S. et al., J Biol Chem 2001; 276: 4889-4893). Additionally vif was shown to be specifically associated with the viral nucleoprotein complex and this might be functionally significant. (Khan M. A. et al., J Virol. 2001; 75 (16): 7252-65). Thus, a vif protein with reduced activity shows a reduced multimerization and/or assoziation to the nucleoprotein complex.

The Vpr protein plays an important role in the viral life cycle. Vpr regulates the nuclear import of the viral preintegration complex and facilitates infection of non dividing cells such as macrophages (Agostini et al., AIDS Res Hum Retroviruses 2002; 18(4):283-8). Additionally, it has transactivating activity mediated by interaction with the LTR (Vanitharani R. et al., Virology 2001; 289 (2):334-42). Thus, a vpr with reduced activity shows decreased or even no transactivation and/or interaction with the viral preintegration complex.

Vpx, which is highly homologous to Vpr, is also critical for efficient viral replication in non-dividing cells. Vpx is packaged in virus particles via an interaction with the p6 domain of the gag precursor polyprotein. Like Vpr Vpx is involved in the transportation of the preintegration complex into the nucleus (Mahalingam et al., J. Virol 2001; 75 (1):362-74). Thus, a Vpx with reduced activity has a decreased ability to associate to the preintegration complex via gag precurser.

The Vpu protein is known to interact with the cytoplasmic tail of the CD4 and causes CD4 degradation (Bour et al., Virology 1995; 69 (3):1510-20). Therefore, Vpu with reduced activity has a reduced ability to trigger CD4 degradation.

The relevant biological activity of the well-characterized Tat protein is the transactivation of transcription via interaction with the transactivation response element (TAR). It was demonstrated that Tat is able to transactivate heterologous promoters lacking HIV sequences other than TAR (Han P. et al., Nucleic Acid Res 1991; 19 (25):7225-9). Thus, a tat protein with reduced activity shows reduced transactivation of promoters via the TAR element.

Nef protein is essential for viral replication responsible for disease progression by inducing the cell surface downregulation of CD4 (Lou T et al., J Biomed Sci 1997;4(4):132). This downregulation is initiated by direct interaction between CD4 and Nef (Preusser A. et al., Biochem Biophys Res Commun 2002;292 (3):734-40). Thus, Nef protein with reduced function shows reduced interaction with CD4.

The relevant function of Rev is the posttranscriptional transactivation initiated by interaction with the Rev-response element (RRE) of viral RNA (Iwai et al., 1992; Nuceic Acids Res 1992; 20 (24):6465-72). Thus, a Rev with reduced activity shows a reduced interaction with the RRE.

The fusion proteins according to the present invention comprise the amino acid sequence of at least four different HIV proteins selected from Vif, Vpr, Vpu, Rev, Vpx, Tat and Nef. The fusion protein may preferably comprise 5, 6 or all of said HIV proteins. The order of the HIV proteins in the fusion protein is not critical.

One or more of the at least four different HIV proteins may be comprised in the fusion protein in two or more copies. Thus, by way of example a fusion protein according to the present invention may comprise Vif, Vpr, Vpu and two copies of Rev. The amino acid sequence of the two or more copies of a HIV protein may be identical. Alternatively, the amino acid sequence of the copies may be different, in particular if protein sequences are used that are derived from different HIV strains or clades (e.g. one copy of an HIV-1 Rev and one copy of an HIV-2 Rev).

Adjacent HIV proteins in the fusion protein may be fused without additional amino acids or fused in such a way that two adjacent HIV proteins in the fusion protein are separated by at least one additional amino acid. Also combinations of both are within the scope of the present invention. By way of example, in a fusion protein according to the present invention comprising the amino acid sequence of four HIV proteins two adjacent HIV proteins may be directly linked to each other, whereas the third and fourth HIV proteins are linked via additional amino acids. The term "additional amino acid" in the context of this embodiment refers to amino acids that are not found in this position in the naturally occurring HIV proteins.

Thus, the fusion protein according to the present invention preferably has the following general formula:

wherein P1 to P7 are different HIV proteins selected from Vif, Vpr, Vpx, Vpu, Tat, Rev and Nef, wherein the fusion protein comprises at least four different of said HIV proteins, i.e. P1 to P4 and optionally one (P5*), two (P5* - - - P6*) or three (P5* - - - P6* - - - P7*) additional of said HIV proteins. The abbreviation "- - -" independently stands for 0 to n additional amino acids. When "- - -" stand for 0 amino acids, the adjacent HIV proteins are directly fused to each other without additional amino acids. When "- - -" stands for 1 to n amino acids the adjacent HIV proteins are separated by one to n amino acids. The upper limit of the additional amino acids, i.e. the integer n, depends on the maximal size of the fusion protein that can be produced or expressed in cells.

According to one embodiment all "- - -" stand independently for 0 to 20, more preferably 0 to 10, even more preferably 0 to 5 additional amino acids.

According to an alternative embodiment at least one of "- - -" stands for the amino acid sequence of an additional protein or a part thereof, which is not an HIV protein selected from Vif, Vpr, Vpx, Vpu, Rev, Tat and Nef. Thus, according to this alternative embodiment the additional protein is flanked by regulatory/accessory HIV proteins. The additional protein may be any protein. More preferably the additional protein comprises additional epitopes that may help to induce a better immune response against HIV. Thus, the additional protein may be the HIV Env, Gag and/or Pol protein or parts thereof. In this context the term "part" of Env, Gag and Pol refers to an amino acid stretch derived from one of said protein, which comprises at least one epitope. More preferably the term part refers to at least 10, even more preferably to at least 20, most preferably to at least 50 amino acids from one of said proteins. According to an related embodiment at least one of "- - -" stands for the amino acid sequence of one or more of the proteins P1 to P7 that are part of the fusion protein. Thus, in this case the fusion protein may comprise one or more copies of one or more of the proteins that are part of the fusion protein. As pointed out the copies of the proteins may or may not have an identical amino acid sequence.

In the above formula the abbreviation "+" independently stands for 0 to n additional terminal amino acid. Thus, the fusion protein according to the present invention may or may not comprise additional amino acids at the C and/or N-terminus of the protein. According to one embodiment at least one of "+" stands for the amino acid sequence of an additional protein or part thereof, which is not an HIV protein selected from Vif, Vpr, Vpx, Vpu, Rev, Tat and Nef. Thus, according to this embodiment the fusion protein comprises at its C and/or N terminus an additional protein, which is not Vif, Vpr, Vpx, Vpu, Rev, Tat or Nef. The additional protein may be any protein. More preferably the additional protein comprises additional epitopes that may help to induce a better immune response against HIV. E.g., the additional protein may be the HIV Env, Gag and/or Pol protein or parts thereof. In this context the term "part" of Env, Gag and Pol refers to an amino acid stretch derived from one of said protein, which comprises at least one epitope. More preferably the term part refers to at least 10, even more preferably to at least 20, most preferably to at least 50 amino acids from one of said proteins.

According to an alternative embodiment at least one of "+" stands for an amino acid sequence that allows the easy detection or purification of the fusion protein. Thus, at least one of "+" might for example be a tag such as a His tag.

According to the present invention the fusion protein is not processed to individual HIV proteins having the natural N- and C-termini. More particularly, the fusion protein according to the present invention is not processed to individual HIV proteins having the natural N- and C-termini, when expressed in human cells. Methods are known to the person skilled in the art how to check whether a fusion protein when expressed in human cells is processed to individual HIV proteins having the natural N- and C-termini. In this context reference is made to Ayyavoo et al., AIDS 2000, 14, 1-9, in particular to the experiment disclosed in FIG. 2 of said publication. Briefly, the person skilled in the art might easily express the respective fusion protein in human cells such as HeLa cells; the cells are then lysed and the cell lysates are subjected to Western blotting experiments or immunoprecipitation assays with antibodies specific for the individual HIV proteins that together form the respective HIV fusion protein. For a fusion protein according to the present invention no significant amount of HIV proteins is detected the size of which corresponds to the size of an individual HIV regulatory/accessory protein.

In order to ensure that the fusion protein according to the present invention is not processed to individual HIV proteins having the natural N- and C-termini, the fusion protein should not contain specific cleavage sequences for cellular proteases, which might trigger the generation of HIV proteins having the natural N- and C-termini, between the amino acid sequences of the HIV proteins that form the fusion protein. Thus, the amino acid sequence "- - -" as abbreviated in the above general formula does not contain specific cleavage sequences for cellular proteases, which might trigger the generation of HIV proteins having the natural N- and C-termini. In particular the fusion protein does not contain the cleavage sequence REKRAVVG (one letter amino acid code) between the amino acid sequences of the different HIV proteins that form the fusion protein. Further cleavage sequences for cellular proteases are known to the person skilled in the art. Thus, the person skilled in the art can easily avoid to include cleavage sequences for (cellular) proteases that might lead to individual HIV proteins having natural N- and C-termini. An example for the cleavage sequence of a cysteinprotease is Ile/leu-X-Thr-X-Gly.

The proteins according to the present invention do not comprise specific cleavage sequences leading to HIV proteins having both, the native N- and C-termini. However, this does not generally exclude the presence of cleavage sites for cellular proteases between the proteins in the fusion protein as long as these cleavage sites do not mediate the generation of HIV proteins having both, a natural N-terminus and a natural C-terminus. In particular, the amino acid sequence "- - -" as abbreviated in the above general formula may comprise cleavage sites for the proteases that are involved in the generation of short peptides presented on MHCI or MHCII. According to this embodiment the result of the cleavage reaction is a short peptide stretch of preferably less than 20 amino acids, the N- or C-terminus of which may correspond to the N- or C-terminus of one of the HIV accessory/regulatory proteins. However, these short peptides, when produced during the process of presentation of antigens, do not have anymore the activity of the HIV protein from which they are derived.

The invention further relates to nucleic acids encoding the above defined fusion proteins according to the present invention. The nucleic acid may be DNA or RNA. Preferably the nucleic acid is DNA if it is intended to insert the nucleic acid into human cells by using a DNA vector such as a plasmid or a vector based on a DNA virus.

Methods are known to the person skilled in the art how to construct a nucleic acid encoding the fusion protein according to the present invention. Without being bound to the following methods, the person skilled in the art may start from a genomic HIV clone, from a subgenomic HIV clone or from any starting material, such as plasmids, comprising the coding sequence of one or more of the regulatory/accessory HIV proteins. If the coding sequence of a regulatory/accessory protein is in the form of a continuous reading frame, said coding sequence may be isolated by cleaving the nucleic acid comprising said coding sequence with appropriate restriction enzymes. The thus obtained DNA fragments may be used for further cloning. Alternatively the coding sequences of an accessory/regulatory protein may be obtained by using Polymerase Chain Reaction (PCR) methods with appropriate primers. If the regulatory/accessory proteins are encoded by more than one exon, as it is the case e.g. for Tat and Rev, it may be necessary to independently clone the different exons and to fuse them to generate a continuous reading frame for the regulatory/accessory protein or to use reverse transcription technology such as RT-PCR.

A coding sequence can also be provided by gene synthesis, i.e. by generating a gene using a set of complementary and/or overlapping oligonucleotides.

In order to obtain a fusion protein the nucleic acid encoding said fusion protein preferably contains a continuous reading frame. Consequently, the stop codons of all but the last sequence encoding HIV proteins or additional proteins are preferably mutated into a codon coding for an amino acid or deleted completely. Preferably, this can be easily achieved if for PCR specific primers are used that amplify the coding sequence without the stop codon. In other words, according to this alternative the downstream primer should not be complementary to the stop codon. The amplified DNA fragment therefore will not contain a stop codon and can be cloned into the cloning vector. Alternatively, it is also possible to clone a coding sequence with its stop codon into the cloning vector. The stop codon can be deleted later, e.g. by using specific endonucleases or by mutagenization.

The result of the cloning steps should be a continuous reading frame encoding the fusion protein according to the present invention.

The regulatory elements that are necessary to obtain the expression of the fusion protein may be any regulatory elements that drive the expression in the desired expression system. If it is intended to produce the fusion protein in prokaryotic cells such as *Escherichia coli* it is preferable to use a bacterial or phage promoter. If it is intended to express the fusion protein in eukaryotic cells it is preferable to use an eukaryotic or viral promoter/enhancer. If it is intended to express the fusion protein by using a poxviral promoter (see below) it is preferable to use a poxviral promoter such as the 7.5 promoter or the ATI promoter.

As pointed out above the fusion protein may comprise fusion partners which are not HIV proteins selected from Vif, Vpr, Vpx, Vpu, Tat, Rev and Nef. Thus, the fusion protein may comprise the amino acid sequence of other proteins or parts thereof. Examples of other proteins are the HIV Gag, Pol and Env proteins. Consequently, the nucleic acid according to the present invention may comprise also the coding sequences for one or more additional proteins or part thereof in the open reading frame encoding at least four regulatory/accessory HIV proteins or derivatives thereof.

In a further embodiment of the present invention the nucleic acid may further comprise independent expression cassettes encoding additional proteins that may help to further improve the immune response against HIV. In a preferred embodiment the nucleic acid may further comprise expression cassettes comprising the coding sequence of at least one additional HIV protein selected from Gag, Pol and Env or parts thereof. Even more preferably the nucleic acid may comprise in addition to the coding sequence of the fusion protein the coding sequences of all HIV proteins Gag, Pol and Env. The nucleic acid is preferably part of a vector. The nucleic acid may also be the viral genome or part thereof of a viral vector, preferably a poxvirus vector such as MVA. Thus, it is possible to express from the poxviral vector the fusion protein as well as the additional HIV proteins, e.g. at least one additional HIV protein selected from Gag, Pol and Env.

The invention further relates to vectors comprising a nucleic acid according to the present invention. The term "vector" refers to any vectors known to the person skilled in the art. A vector can be a plasmid vector such as pBR322 or a vector of the pUC series. More preferably the vector is a virus vector. In the context of the present invention the term "viral vector" or "virus vector" refers to an infectious and/or attenuated virus comprising a viral genome. In this case the nucleic acid of the present invention is part of the viral genome of the respective viral vector and/or constitutes the viral genome. The recombinant vectors can be used for the infection of cells and cell lines, in particular for the infection of living animals including humans. Typical virus vectors according to the present invention are adenoviral vectors, retroviral vectors or vectors on the basis of the adeno associated virus 2 (AAV2). Most preferred are poxviral vectors. The poxvirus may be preferably a canarypox virus, a fowlpoxvirus or a vaccinia virus. More preferred is modified vaccinia virus Ankara (MVA) (Sutter, G. et al. [1994], Vaccine 12: 1032-40). A typical MVA strain is MVA 575 that has been deposited at the European Collection of Animal Cell Cultures under the deposition number ECACC V00120707. Most preferred is MVA-BN or a derivative thereof, which has been described in the PCT application PCT/EP01/13628 filed at the European Patent Office on Nov. 22, 2001, entitled "Modified Vaccinia Ankara Virus Variant". MVA-BN has been deposited at the European Collection of Animal Cell Cultures with the deposition number ECACC V00083008. By using MVA-BN or a derivative thereof the additional technical problem has been solved to provide a particular safe virus vaccine against HIV since the MVA-BN virus vector is an extremely attenuated virus, which is derived from Modified Vaccinia Ankara virus and which is characterized by the loss of its capability to reproductively replicate in human cells. MVA-BN is safer than any other known vaccinia virus strains due to a lack of replication in humans. In a preferred embodiment the invention concerns as a viral vector containing the DNA according to the present invention MVA-BN and derivatives of MVA-BN. The features of MVA-BN, the description of biological assays allowing to evaluate whether a MVA is MVA-BN or a derivative thereof and methods allowing to obtain MVA-BN or a derivative thereof are disclosed in the above referenced PCT application PCT/EP01/13628, which is herewith incorporated by reference.

Thus, according to these embodiments the invention concerns preferably a recombinant MVA, such as MVA-BN, comprising in the viral genome an expression cassette encoding a fusion protein according to the present invention.

Methods to insert the nucleic acid according to the present invention into the viral genome and methods to obtain recombinant viruses are known to the person skilled in the art.

In a recombinant vaccinia virus the expression of the DNA according to the present invention is preferably, but not exclusively, under the transcriptional control of a poxvirus promoter, more preferably of a vaccinia virus promoter. The insertion of the DNA according to the present invention is preferably into a non-essential region of the virus genome. In another preferred embodiment of the invention, the heterologous nucleic acid sequence is inserted at a naturally occurring deletion site of the poxviral genome (disclosed in PCT/EP96/02926). However, the nature of the insertion site is not critical for the present invention as long as a recombinant Vaccinia virus is obtained. Thus, the person skilled in the art may easily envisage further suitable insertion sites.

Preferably the viral vector, in particular the poxviral vector may comprise additional retroviral genes selected from HIV Gag, Pol and Env genes in the viral genome, in addition to the coding sequence for the fusion protein according to the present invention. More preferably the viral vector, in particular the poxviral vector, may comprise all HIV genes encoding Gag, Pol and Env in addition to the coding sequence for the fusion protein according to the present invention. These additional genes might have been inserted with the same nucleic acid according to the present invention. According to this embodiment all HIV genes would be located in the same insertion site in the viral genome. In an alternative embodiment the additional genes are inserted in different locations of the viral genome.

In a preferred embodiment the present invention concerns the nucleic acid, the vector or the fusion protein according to the present invention as a vaccine for the at least partial prophylaxis against HIV infections and AIDS. A "vaccine" is a compound, i.e. a nucleic acid, a fusion protein, a vector or a virus that induces a specific immune response.

According to one alternative of this embodiment the "vaccine" according to the present invention is based on the fusion protein according to the present invention.

In a preferred embodiment the nucleic acid according to the present invention, in particular DNA, is used as a vaccine. It is known by the person skilled in the art that the administration of naked DNA harboring a eukaryotic expression cassette as in the present invention, in particular the intramuscular injection of DNA leads to the expression of the protein encoded by the expression cassette. The protein is exposed to the immune system and a specific immune response is raised.

In an alternative embodiment the vaccination is made by administering a vector according to the present invention, in particular a viral vector, more preferably a poxvirus vector, most preferably a vaccinia virus vector, e.g. a MVA vector.

For the preparation of a vaccinia virus based vaccine, the virus according to the invention is converted into a physiologically acceptable form. This can be done based on the experience in the preparation of poxvirus vaccines used for vaccination against smallpox (as described by Stickl, H. et al. [1974] Dtsch. med. Wschr. 99, 2386-2392). For example, the purified virus is stored at −80° C. with a titer of $5 \times 10^8$ $TCID_{50}$/ml formulated in about 10 mM Tris, 140 mM NaCl pH 7.4. For the preparation of vaccine shots, e.g., $10^2$-$10^8$ particles of the virus are lyophilized in 100 ml of phosphate-buffered saline (PBS) in the presence of 2% peptone and 1% human albumin in an ampoule, preferably a glass ampoule. Alternatively, the vaccine shots can be produced by stepwise freeze-drying of the virus in a formulation. This formulation can contain additional additives such as mannitol, dextran, sugar, glycine, lactose or polyvinylpyrrolidone or other additives such as antioxidants or inert gas, stabilizers or recombinant proteins (e.g. human serum albumin) suitable for in vivo administration. The glass ampoule is then sealed and can be stored between 4° C. and room temperature for several months. However, as long as no need exists the ampoule is stored preferably at temperatures below −20° C. For vaccination the lyophilisate can be dissolved in 0.1 to 0.5 ml of an aqueous solution, preferably physiological saline or Tris buffer, and administered either systemically or locally, i.e. by parenterally, intramuscularly or any other path of administration know to the skilled practitioner. The mode of administration, the dose and the number of administrations can be optimized by those skilled in the art in a known manner. Most preferred for poxvirus vectors is subcutaneous or intramuscular administration.

If the vaccine is a MVA-BN vector or derivative thereof comprising a DNA according to the present invention, a particular embodiment of the present invention concerns the administration of the vaccine in therapeutically effective amounts in a first inoculation ("priming inoculation") and in a second inoculation ("boosting inoculation").

If the vaccine is a MVA-BN vector or derivative thereof comprising a DNA according to the present invention a particular embodiment of the present invention concerns a kit for vaccination comprising a MVA-BN virus vector according to the present invention for the first vaccination ("priming") in a first vial/container and for a second vaccination ("boosting") in a second vial/container.

Thus the invention concerns in the vaccine embodiments a vaccine comprising a nucleic acid, a vector or a fusion protein according to the present invention and the use of said nucleic acid, vector or protein for the preparation of a vaccine.

According to a further embodiment the invention concerns a method for protecting an animal, including a human, against an HIV infection by administering to an animal, including a human, in need thereof a fusion protein according to the present invention, a nucleic acid according to the present invention or a vector according to the present invention.

Moreover, the invention concerns a method of producing a protein according to the present invention, comprising the steps of (i) transfecting a host cell with a nucleic acid or a vector according to the present invention or (ii) infecting a host cell with a viral vector according to the present invention, (iii) expressing the fusion protein in the transfected host cell of step (i) or the infected host cell of step (ii), and (iv) recovering the fusion protein.

The invention further relates to host cells transfected with a nucleic acid or a vector according to the present invention or infected with a viral vector according to the present invention.

According to an alternative embodiment the fusion protein may comprise at least three different HIV proteins selected from Vif, Vpr, Vpu, Rev, Vpx and Tat. The fusion protein may preferably comprise 4, 5 or all of said HIV proteins. A typical fusion protein according to this embodiment comprises the amino acid sequence of the HIV proteins Vpr, Vif, Vpu, Rev and Tat or derivatives of the amino acid sequence of one or more of said proteins. As pointed out above, the order of the HIV proteins in the fusion protein is not critical. All preferred embodiments as specified above also apply for this alternative embodiment.

SHORT DESCRIPTION OF THE FIGURES

The picture shows the annealing of four Oligonucleotides. They are single stranded and can be annealed by complementary ends. The gaps are filled in with a polymerase, which exhibits a proofreading activity (eg Pfx polymerase).

The vif gene shows a overlapping sequence with the vpr fragment, the vpu coding fragment shows an overlapping sequence with the rev gene (grey). The PCR fragments are denatured and the overlapping complementary ends are hybridized. The resulting gaps are filled using Pfx polymerase. The vif-vpr fragment is fused to a overlapping sequence of the vpu-rev fragment, which again is used for fusion.

FIG. 3: Cloning strategy of the sequence encoding a fusion protein according to the present invention in a recombination vector for insertion of foreign genes into the MVA genome The fused vif, vpr, vpu and rev polyprotein coding region was amplified with primers comprising a ClaI and ApaI restriction site. This pCR product was cloned into the ClaI/ApaI cutted vector pBNX65, which contains the Poxvirus ATI promoter. The tat coding region was amplified by PCR with primers containing an Acc65I restriction site and ligated to the Acc65I linearized pBNX65+vif-rev. The resulting expression cassette (ATI promoter+sequence encoding a fusion protein according to the present invention) was isolated by PacI restriction and inserted in the recombination vector for insertion of foreign genes in the MVA genome I4L intergenic region (pBNX39). PBNX39 contains sequences homologous to the flanking sequences of the insertion site of the MVA genome (F1 I4L and F2 I4L). For selection of recombinant viruses after homologous recombination of the MVA genome and pBNX39 the vector additionally contains the *E. coli* gpt gene (phosphoribosyltransferase gene). After purification of recombinant viruses, the selection cassette is deleted by homologous recombination between Flank 1 and a repeat sequence of flank 1 (F1rpt).

FIG. 4: Schematic presentation of the MVA genome

MVA contains a linear genome, which shows characteristic fragments after restriction with Hind III (A-O). The non functional region between the I4L and the I5L genes is located in the I fragment. Insertion of foreign genes using pBNX39 occurs at position 56767-56768.

EXAMPLES

Generation of a DNA Encoding a HIV Vif-Vpr-Vpu-Rev-Tat Fusion Protein

The single genes of the HIV genome were either prepared by PCR out of genomic DNA by using standard PCR protocols or synthetically by a technique, which is based on the annealing of oligonucleotides via overlapping sequences and fill in of the resulting single stranded gaps.

For the oligonucleotide based generation of coding regions of genes, which are to be inserted into the nucleic acid encoding the fusion protein according to the present invention, 40 mer oligonucleotides with 15 bp overlaps were designed. The sequence of the oligonucleotides is based on the genomic map of the HIV1 isolate HXB2R that is derived from strain IIIB. The oligonucleotides for the annealing reaction or the PCR for isolation of the required sequence were designed in that way, that in the resulting coding region the stop codons for translation termination were deleted. The tat gene was synthesized using oligos containing a Stop codon as this gene was to be inserted at the last postion of the nucleic acid encoding the fusion protein according to the present invention and therefore should contain a stop triplet for a correct termination of translation of the polyprotein.

For the oligoannealing rection 10 cycles of a two step Pfx polymerase (Gibco-BRL) reaction (denaturation at 95° C. and annealing/extension at 68° C.) were performed. During that reaction the overlapping sequences of the oligos become annealed and the gaps are filled in by Pfx proofreading polymerase (FIG. 1).

For synthesis of the vif coding region, the first encoded gene in the nucleotide sequence encoding the fusion protein, a PCR using genomic HIV cDNA was performed. The PCR was performed in that way, that the vif coding region was fused to the first 15 bp of the following vpr gene for the subsequent annealing of vif and vpr. The Vpr coding region, which covers bp 5559-5847 of the HIV HXB2R genome, was prepared by annealing of 10 oligonucleotides. The resulting gaps were filled and after subsequent PCR for amplification the product contained the vpr coding region fused to flanking regions for vif and vpu, which was to be inserted after vpr coding region.

The Vpu coding region was amplified by PCR out of the same cDNA used for synthesis of vif and the resulting product contained the flanking regions for fusion with vpr and rev.

The rev coding region was synthesized by annealing of 14 oligonucleotides, which cover the region bp 5970-6045 and 8379-8650 of the HIV HXB2R genome and 15 bp overlaps for annealing with vpu and tat.

The tat coding region was created by using 10 oligonucleotides, which cover bp 5831-6045 and 8379-8466 of the HIV HXB2R genome.

Figure 1:
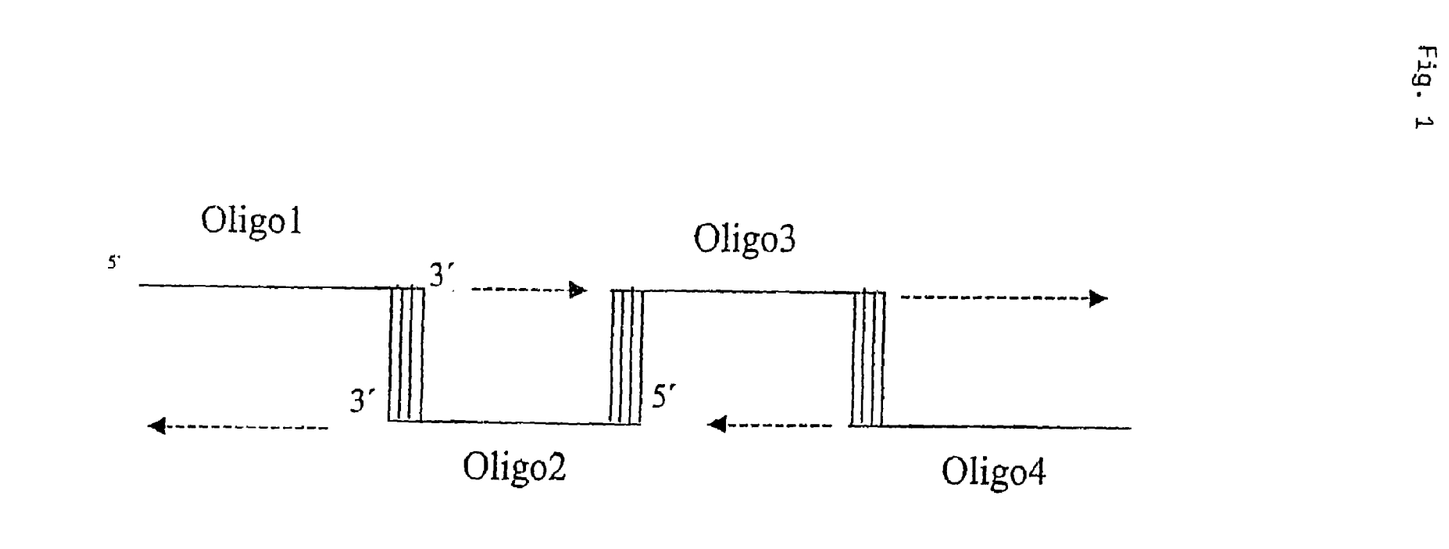
FIG. 1: Schematic presentation of Annealing of Oligonucleotides
Figure 2:
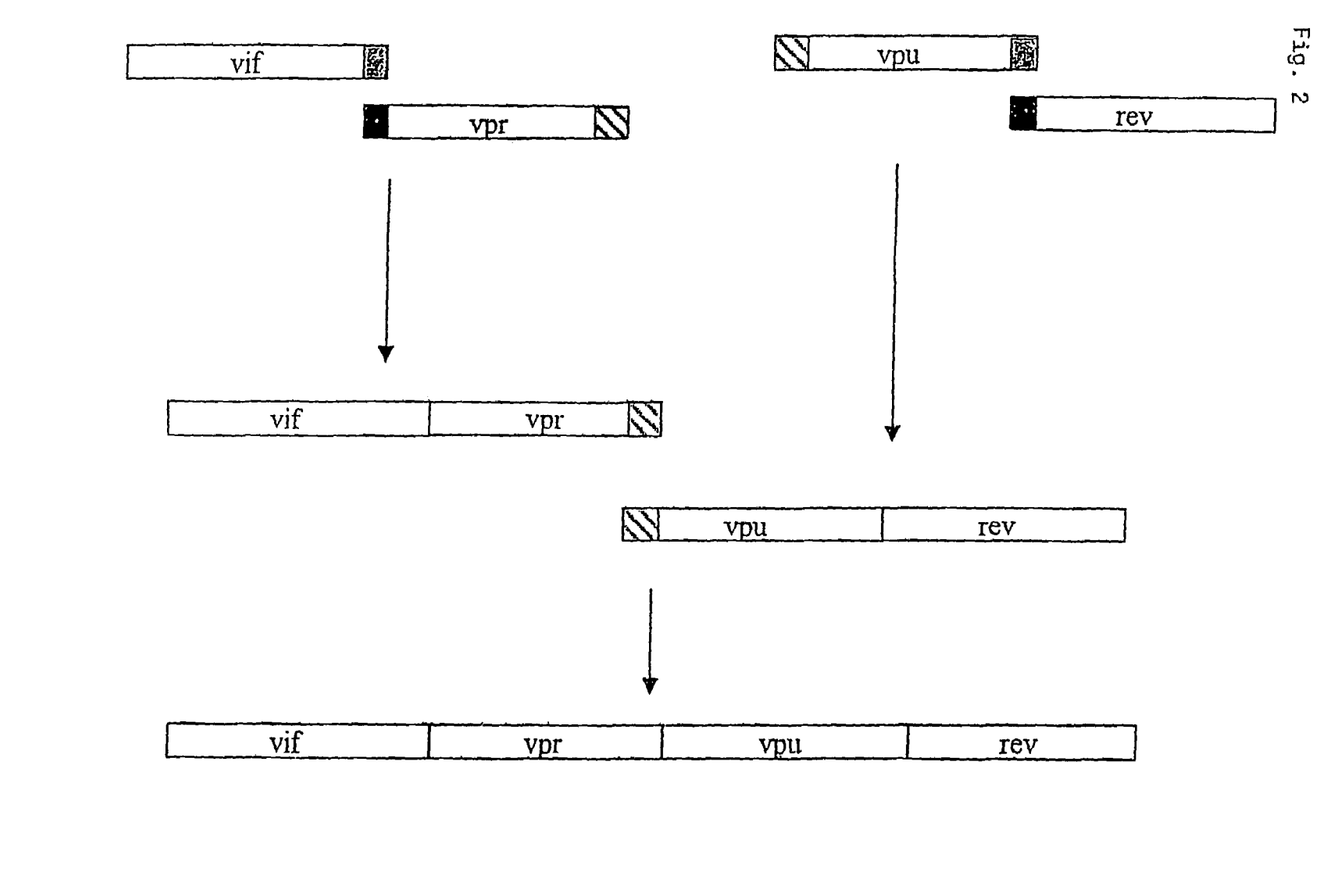
FIG. 2: Schematic presentation of annealing of four genes of the blob
Figure 3:
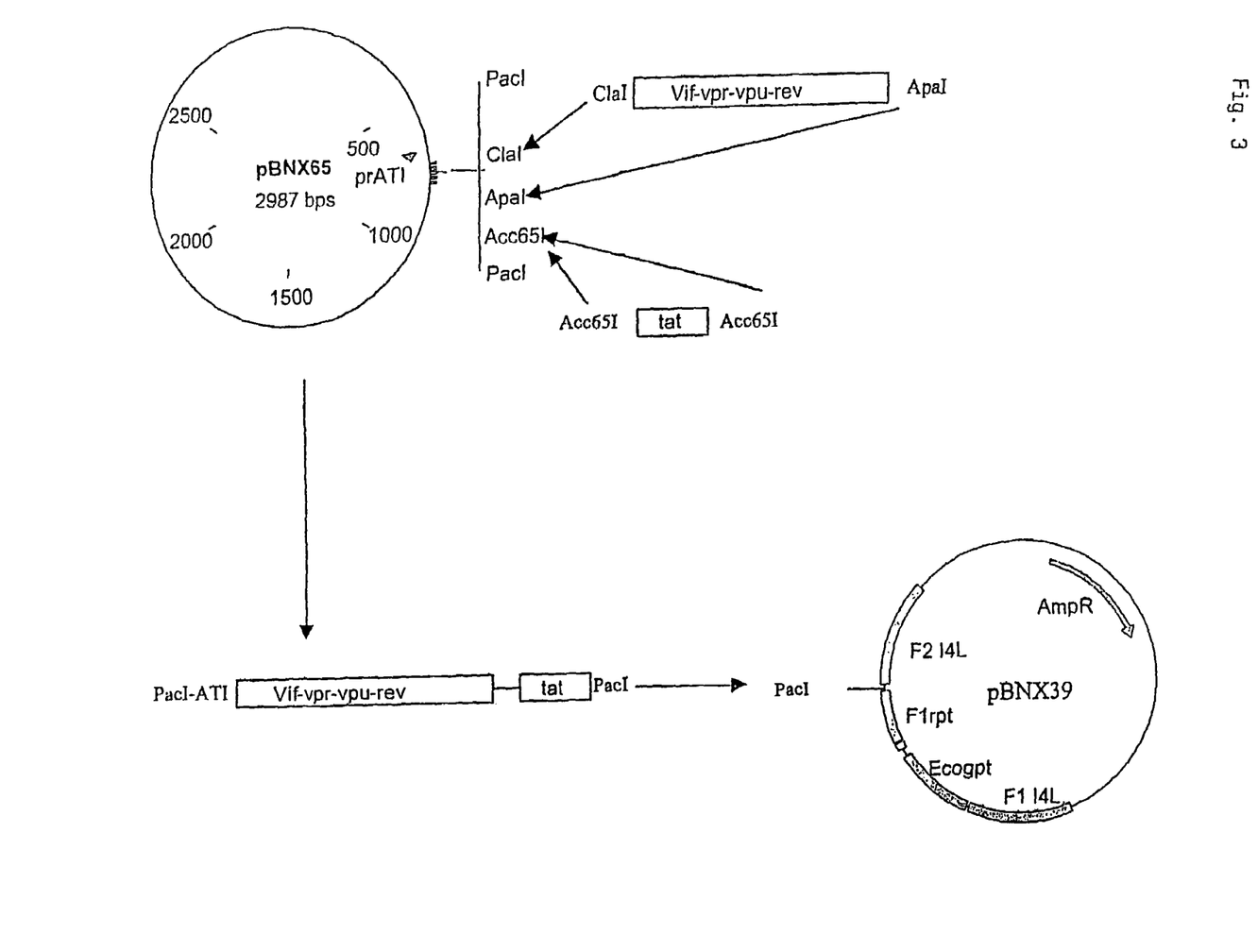
Figure 4:
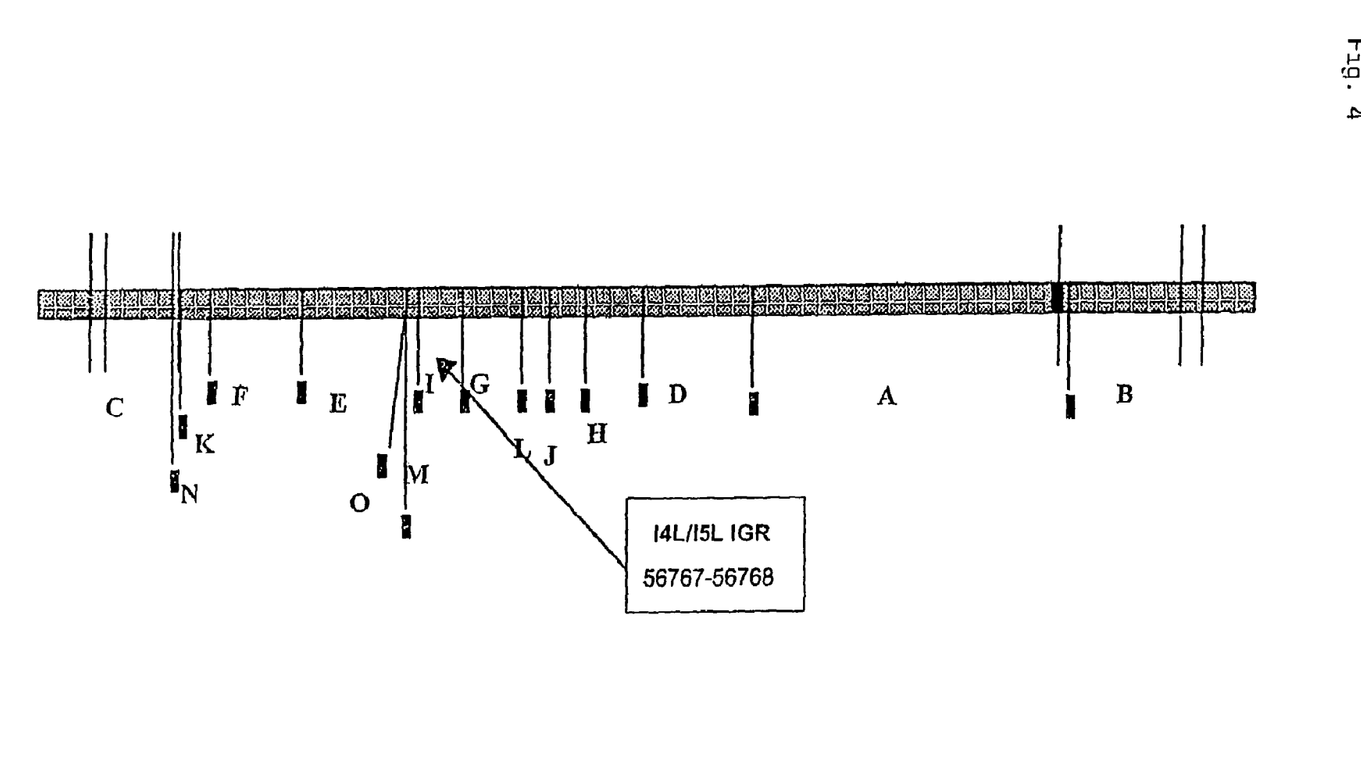

The vif and the vpr coding region as well as the vpu and the rev coding region were fused by annealing of the two fragments via their overlaps with a two step Pfx polymerase reaction (FIG. 2). After additional PCR amplification of the fusion products, the fragments were purified and ligated to each other via the overlap of vpr and vpu (FIG. 2). After PCR amplification of the resulting product (coding sequences for vif-vpr-vpu-rev) the tat coding region was fused by cloning of the vif-vpr-vpu-rev fragment and tat in adjacent cloning sites in a pBluescriptKS+vector containing the poxvirus ATI promoter (FIG. 3, pBNX65). The complete expression cassette was then isolated by PacI restriction and inserted in pBNX39 (FIG. 3). PBNX39 contains sequences homologous to the MVA genome, which allows insertion in a non coding region (I4L) of the genome (FIG. 4) by homologous recombination.

What is claimed is:

1. A Vaccinia virus vector comprising a nucleic acid encoding a fusion protein,
    wherein the fusion protein comprises an amino acid sequence of at least four non-attenuated HIV regulatory and accessory proteins selected from the group consisting of Vif, Vpr, Vpu, Vpx, Rev, Tat, and Nef, wherein the regulatory and accessory proteins are not separated by specific cleavage sequences for a cellular protease, thereby avoiding processing to yield regulatory and accessory proteins with native N- and C-termini.

2. The Vaccinia virus vector of claim 1, wherein the expression of the fusion protein from the DNA is controlled by a poxviral promoter.

3. The Vaccinia virus vector of claim 1, wherein the nucleic acid further comprises the coding sequence for at least one additional HIV protein selected from the group consisting of Gag, Pol and Env.

4. The Vaccinia virus vector of claim 3, wherein the nucleic acid comprises the coding sequence for the HIV Gag, Pol and Env proteins.

5. The Vaccinia virus vector of claim 1, wherein the nucleic acid encodes a fusion protein Vif-Vpr-Vpu-Rev-Tat.

6. The Vaccinia virus vector of claim 1, wherein the nucleic acid encodes a fusion protein Vif-Vpr-Vpu-Rev.

7. The Vaccinia virus vector of claim 1, wherein the Vaccinia virus vector is Modified Vaccinia Virus Ankara (MVA).

8. A host cell infected with the Vaccinia virus vector of claim 1.

* * * * *